United States Patent [19]

Clemence et al.

[11] 4,172,137

[45] * Oct. 23, 1979

[54] 5-THIAZOLE-ALKYLAMINES USED AS ANTILIPOLYTICS

[75] Inventors: François Clémence; Robert Fournex, both of Paris, France

[73] Assignee: Roussel UCLAF, Paris, France

[*] Notice: The portion of the term of this patent subsequent to Aug. 22, 1995, has been disclaimed.

[21] Appl. No.: 820,098

[22] Filed: Jul. 29, 1977

[30] Foreign Application Priority Data

Aug. 11, 1976 [FR] France .............................. 76 24496

[51] Int. Cl.² .......................................... A61K 31/425
[52] U.S. Cl. .................................. 424/270; 548/202; 548/204
[58] Field of Search ..................... 260/302 R; 424/270

[56] References Cited

U.S. PATENT DOCUMENTS 4,108,994  8/1978  Poitteuin et al. ................. 260/302 R

FOREIGN PATENT DOCUMENTS 2073427 10/1971 France .
2242094 3/1975 France .
1149110 4/1969 United Kingdom ................ 260/302 R

OTHER PUBLICATIONS

White, et al., "Principles of Biochemistry", 1968, p. 526.
Buchman, et al., Chem. Abstracts, 39:18713, (1945).
Wagner, et al., Synthetic Organic Chemistry, John Wiley & Sons, N.Y., 1953, pp. 666–670 and 679–680.
Zubarovskii, et al., Chem. Abstracts, 58:2525, (1963).

Primary Examiner—David Wheeler
Attorney, Agent, or Firm—Hammond & Littell

[57] ABSTRACT

Novel 5-thiazole-alkylamines of the formula

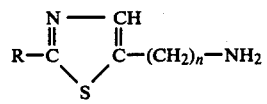

wherein R is alkyl of 1 to 6 carbon atoms and n is a whole number of 2 to 7 and their non-toxic, pharmaceutically acceptable acid addition salts having marked antilipolytic activity.

3 Claims, No Drawings

5-THIAZOLE-ALKYLAMINES USED AS ANTILIPOLYTICS

STATE OF THE ART

French Pat. No. 2,073,427 and No. 2,242,094 describe different thiazole derivatives.

OBJECTS OF THE INVENTION

It is an object of the invention to provide the novel compounds of formula I and their non-toxic, pharmaceutically acceptable acid addition salts.

It is another object of the invention to provide a novel process for the preparation of compounds of formula I and to novel intermediates therefore.

It is a further object of the invention to provide novel antilipolytic compositions as well as a novel method of reducing the level of plasmatic free fatty acids in the blood of warm-blooded animals.

These and other objects and advantages of the invention will become obvious from the following detailed description.

THE INVENTION

The novel 5-thiazole-alkylamines of the invention have the formula

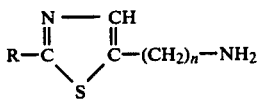

wherein R is alkyl of 1 to 6 carbon atoms and n is a whole number of 2 to 7 and their non-toxic, pharmaceutically acceptable acid addition salts.

Examples of suitable alkyl substituents of R are methyl, ethyl, n-propyl, isopropyl, n-butyl, isobutyl, tert.-butyl, pentyl and hexyl.

Examples of suitable acids for the preparation of the acid addition salts are inorganic acids such as hydrochloric acid, hydrobromic acid, hydroiodic acid, nitric acid, sulfuric acid, or phosphoric acid and organic acids such as acetic acid, maleic acid, fumaric acid, succinic acid, tartaric acid, oxalic acid, alkylsulfonic acids such as methanesulfonic acid, ethanesulfonic acid, propane sulfonic acid, alkyldisulfonic acids such as methanedisulfonic acid, $\alpha,\beta$-ethane disulfonic acid, $\alpha,\beta$-propane disulfonic acid, arylmonosulfonic acids such as benzene sulfonic acid and aryldisulfonic acids. The compounds of formula I may be salified with one equivalent of acid or if the acid is sufficiently strong with two equivalents of acid.

Among the preferred compounds of formula I and its acid addition salts are those wherein n is an odd whole number. A preferred compound is 2-methyl-5-thiazole-propanamine and its hemisuccinate.

The novel process of the invention for the preparation of a compound of formula I comprises reacting a compound of the formula

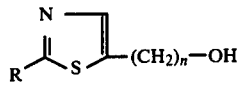

wherein R and n have the above definitions with a chlorination or bromination agent to obtain a compound of the formula

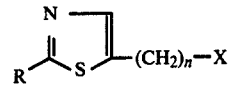

wherein X is bromine or chlorine, reacting the latter with an alkali metal phthalimide to obtain a compound of the formula

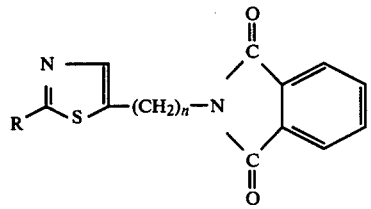

and treating the latter with a strong acid to obtain a compound of formula I in its acid addition salt form and optionally treating the latter with a base to obtain the compound of formula I which may be salified, if desired.

In a preferred mode of the process, the compound of formula II is reacted with a halogenation agent such as thionyl chloride, phosphorus pentachloride or phosphorus tribromide in an organic solvent such as benzene, toluene, tetrahydrofuran or cyclohexane. The alkali metal phthalimide may be sodium, potassium or lithium phthalimide and the reaction is preferably effected in an organic solvent such as chloroform, benzene, toluene, ether, tetrahydrofuran, cyclohexane or dimethylformamide at room temperature to reflux.

The strong acid used to treat the compound of formula IV is preferably a strong inorganic acid such as hydrochloric acid, hydrobromic acid, phosphoric acid or sulfuric acid in an aqueous media although equally useful are aqueous-alcoholic solutions with a lower alkanol such as methanol, ethanol or isopropanol. The base used to treat the salified compound of formula I may be sodium hydroxide, potassium hydroxide, sodium carbonate, potassium carbonate, ammonium hydroxide etc. preferably in an organic solvent such as ethyl acetate, chloroform or methylene chloride.

The novel antilipolytic compositions of the invention are comprised of an antilipolytically effective amount of at least one compound of formula I and its non-toxic, pharmaceutically acceptable acid addition salts and an inert pharmaceutical carrier. The compositions may be in the form of tablets, gelules, granules, suppositories and injectable solutions or suspensions formed in the usual manner.

Examples of suitable excipients for the compositions are talc, arabic gum, lactose, starch, magnesium stearate, cacao butter, aqueous and non-aqueous vehicles, fatty bodies of animal or vegetable origin, paraffinic derivatives, glycols, preservatives, diverse wetting agents, emulsifiers and dispersants.

The compositions are useful for the treatment of acute or chronic hyperlipemia, coronary insufficiencies, cardiac insufficiencies of atheromatos origin and chronic anginic states. A preferred composition contains 2-methyl-5-thiazole-propamine and its hemisuccinate.

The novel method of the invention for inducing antilipolytic activity in warm-blooded animals, including humans, comprises administering to warm-blooded animals an antilipolytically effective amount of at least one compound of the formula

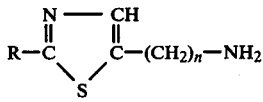   I wherein R is alkyl of 1 to 6 carbon atoms and n is a whole number of 2 to 7 and their non-toxic, pharmaceutically acceptable acid addition salts. The products may be administered orally, rectally or parenterally and the usual daily dose is 2 to 50 mg/kg when administered orally.

The novel intermediate products of the invention have the formula

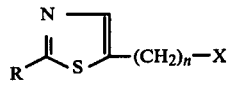

wherein R is alkyl of 1 to 6 carbon atoms, n is a whole number from 2 to 7 and X is chlorine or bromine.

The compounds of formula II may be prepared by reducing a compound of the formula

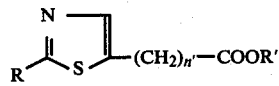   V wherein R has the above definition, n' is a whole number from 1 to 6 and R' is alkyl of 1 to 6 carbon atoms with a reducing agent such as lithium aluminum hydride in an organic solvent.

The compounds of formula V may be prepared by reacting an alkyl thioamide of the formula

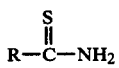

wherein R has the above definition in an organic solvent with a compound of the formula

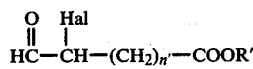

wherein Hal is chlorine or bromine and n' and R' have the above definition.

The compounds of formula V wherein n' is 2 may also be prepared by reacting a compound of the formula

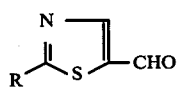

wherein R is alkyl of 1 to 6 carbon atoms with malonic acid in the presence of a basic agent to obtain a compound of the formula

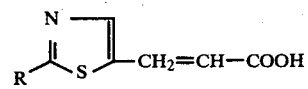

which is then treated with a reducing agent such as hydrogen with palladium present to obtain a compound of the formula

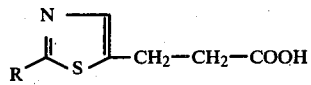

which is then reacted with an alcohol of the formula R'OH wherein R' has the above definition.

In the following examples there are described several preferred embodiments to illustrate the invention. However, it should be understood that the invention is not intended to be limited to the specific embodiments.

EXAMPLE 1

Hemisuccinate of 2-methyl-5-thiazole-propanamine

STEP A: 3-(2-methyl-5-thiazolyl)-2-propenoic acid

A mixture of 29 g of 2-methyl-5-thiazole-carboxaldehyde, 30 ml of pyridine, 29 g of malonic acid and 30 drops of piperidine was heated at 100°–110° C. for 5 hours and was then cooled to room temperature and was poured into 500 ml of water. The pH of the solution was adjusted to 3 with N sulfuric acid and the mixture was vacuum filtered. The recovered precipitate was dried to obtain 27.8 g of product which was crystallized from 800 ml of water containing 10% of ethanol to obtain 23.8 g of 3-(2-methyl-5-thiazolyl)-2-propenoic acid melting at 204° C.

STEP B: 2-methyl-5-thiazole-propanoic acid

A mixture of 10 g of 3-(2-methyl-5-thiazolyl)-2-propenoic acid, 260 ml of ethanol, 15 ml of triethylamine and 5 g of 10% palladized activated carbon was held under hydrogen for one hour and was then vacuum filtered. The catalyst was rinsed with ethanol and the filtrate was evaporated to dryness to obtain 13.3 g of a colorless oil. The oil was dissolved in 100 ml of water and anhydrous sulfurous acid was bubbled through the solution until the pH was acidic. Nitrogen was then bubbled therethrough and the mixture was vacuum filtered. The crystals recovered were washed and dried to obtain 7.1 g of product which was crystallized from ethyl acetate to obtain 6.5 g of 2-methyl-5-thiazole-propanoic acid melting at 120° C.

STEP C: methyl 2-methyl-5-thiazole-propanoate

A mixture of 31.7 g of the product of Step B, 3.2 ml of concentrated sulfuric acid and 300 ml of methanol was refluxed for 16 hours and was evaporated to dryness under reduced pressure. The residue was taken up in 100 ml of water and concentrated ammonium hydroxide was added thereto to adjust the pH to 12–13. The mixture was extracted with methylene chloride and the extracts were dried over magnesium sulfate and evaporated to dryness under reduced pressure to obtain 35 g of raw methyl 2-methyl-5-thiazole-propanoate. Reaction with hydrochloric acid resulted in the hydrochloride melting at 115° C.

STEP D: 2-methyl-5-thiazole-propanol

A solution of 10.9 g of methyl 2-methyl-5-thiazole-propanoate in 70 ml of tetrahydrofuran was slowly added with stirring at 10° to 15° C. to a mixture of 3.42 g of lithium aluminum hydride in 125 ml of tetrahydrofuran and the mixture was stirred for about 30 minutes. Tetrahydrofuran containing 20% of water was slowly added to the mixture which was then filtered. The residue was washed with ethyl acetate; the filtrate was dried over magnesium sulfate and evaporated to dryness to obtain 8.4 g of raw product which was rectified under reduced pressure to obtain 6.4 g of 2-methyl-5-thiazole-propanol with a boiling point of 106° C. at 0.05 mm Hg.

Analysis: $C_7H_{11}NOS$. Calculated: %C 53.47, %H 7.05, %N 8.90, %S 20.39. Found: %C 53.2, %H 7.2, %N 8.6, %S 20.1.

STEP E: 2-methyl-5-thiazole-3-chloropropyle 12.7 ml of thionyl chloride were slowly added with stirring to a mixture of 13.7 g of 2-methyl-5-thiazole-propanol and 150 ml of anhydrous benzene cooled on an ice bath to 10°–12° C. and the mixture was stirred at room temperature for 48 hours. The solution was then poured into 300 ml of ice and a solution saturated with sodium carbonate was added to adjust the pH to 7–8. The aqueous phase was decanted and was extracted with ethyl acetate. The combined ethyl acetate phases were dried over magnesium sulfate, was filtered and evaporated under reduced pressure to obtain 15 g of 2-methyl-5-thiazol-3-chloropropyle in the form of a brown oil.

STEP F: 2-[(2-methyl-thiazol-5-yl)-propyl]-1H-isoindole-1,3-(2H)-dione

A mixture of 15 g of the product of Step E, 45 ml of dimethylformamide and 16 g of the potassium salt of 1H-isoindole-1,3-(2H)-dione was refluxed for 4 hours and then 450 ml of water were added. The mixture was vacuum filtered and the recovered precipitate was washed with water and dried to obtain 20 g of 2-[(2-methyl-thiazol-5-yl)-propyl]-1H-isoindole-1,3-(2H)-dione melting at 75° C.

STEP G: hemisuccinate of 2-methyl-5-thiazole-propanamine

A solution of 19 g of the product of Step F in 100 ml of concentrated hydrochloric acid was refluxed for 16 hours and was then iced. Concentrated sodium hydroxide solution was slowly added thereto to adjust the pH to 12–13 and the mixture was extracted with ethyl acetate. The extracts were dried and evaporated to dryness under reduced pressure to obtain 11 g of raw product which was dissolved in ethyl acetate. A solution of 10% succinic acid in methanol was added thereto until the pH was 7 and the mixture was iced and vacuum filtered. The recovered product was dried and was crystallized from isopropanol to obtain 11.8 g of the hemisuccinate of 2-methyl-5-thiazole-propanamine melting at 170° C.

Analysis: $C_{19}H_{15}N_2O_2S$. Calculated: %C 50.21, %H 7.02, %N 13.01, %S 14.89. Found: %C 50.1, %H 7.1, %N 12.9, %S 14.6.

EXAMPLE 2 ethyl 2-methyl-5-thiazole-acetate

A mixture of 28.7 g of ethyl 3-bromo-4-oxo-butylrate, 300 ml of dichloroethane and 11.2 g of thioacetamide was refluxed with stirring and dichloroethane was added thereto to keep the volume constant. After 10 hours, the mixture returned to room temperature and was evaporated to dryness. The residue was taken up in ethyl acetate and the solution was extracted with 2 N hydrochloric acid. The pH of the aqueous extracts was adjusted to alkaline by addition of ammonium hydroxide and the aqueous phase was extracted with ethyl acetate. The ethyl acetate extracts were washed with water, dried and concentrated to dryness to obtain 8.3 g of ethyl 2-methyl-thiazole-acetate.

IR Spectrum ($CHCl_3$): C=O ester at $1737^{cm-1}$, C=C and C=N at $1535^{cm-1}$.

EXAMPLE 3

Tablets were prepared containing 300 mg of the hemisuccinate of 2-methyl-5-thiazol-propanamine and an excipient of lactose, wheat starch, treated starch, rice starch, talc and magnesium stearate as well as gelules containing 300 mg of the said hemisuccinate and an excipient of talc, aerosil and magnesium stearate.

PHARMACOLOGICAL STUDY

A. Acute Toxicity

The acute toxicity was determined on groups of 10 mice weighing 18 to 22 g with the product of Example 1 being administered intraperitoneally in suspension in carboxymethylcellulose and the animals were observed for one week. The $DL_{50}$ dose was determined to be 550 mg/kg under these conditions.

B. Antilipolytic Activity

Male rats of the Sprague Dawley S.P.F. strain weighing 180 to 200 g were held without food and water for 24 hours and then orally received the product of Example 1. One hour after the administration, the rats were killed and blood samples were taken to determine the amount of free fatty acids. The extraction of the free fatty acids was effected by the technique of Dole [J. Clin. Invest., Vol. 38 (1959), pp. 1544–1554] modified by Trout, et al, [J. Lipid. Res., Vol. 1 (1960), pp. 199–202]. The plasmatic extract free of phospholipids was colorimetrically determined by the method of Anthonis, [J. Lipid. Res., Vol. 6 (1965), pp. 307–312]. The dose of the said product which diminished by 50% the level of the free fatty acids as compared to the control animals was determined under these conditions to be ≃1 mg/kg.

Various modifications of the products and process of the invention may be made without departing from the spirit or scope thereof and it is to be understood that the invention is intended to be limited only as defined in the appended claims.

We claim:

1. A method of inducing antilipolytic activity in warm-blooded animals comprising administering to warm-blooded animals an antilipolytically effective amount of at least one compound of the formula $$R-C\underset{S}{\overset{N-CH}{\underset{\diagdown\quad\diagup}{\parallel\quad\parallel}}}C-(CH_2)_n-NH_2$$

wherein R is alkyl of 1 to 6 carbon atoms and n is a whole number of 2 to 7 and their non-toxic, pharmaceutically acceptable acid addition salts.

2. The method of claim 1 wherein n is an odd whole number.

3. The method of claim 1 wherein the compound is selected from the group consisting of 2-methyl-5-thiazolepropanamine and its hemisuccinate.

* * * * *